United States Patent [19]

Cantor et al.

[11] Patent Number: 5,561,043
[45] Date of Patent: Oct. 1, 1996

[54] SELF-ASSEMBLING MULTIMERIC NUCLEIC ACID CONSTRUCTS

[75] Inventors: Charles R. Cantor, Boston, Mass.; Christof M. Niemeyer, Bremen, Germany; Cassandra L. Smith, Mass.; Takeshi Sano, both of Boston, Mass.; Donald J. Hnatowich, Brookline, Mass.; Mary Rusckowski, Southborough, Mass.

[73] Assignee: Trustees of Boston University, Boston, Mass.

[21] Appl. No.: 189,448

[22] Filed: Jan. 31, 1994

[51] Int. Cl.[6] ............................ C12Q 1/68; C07H 21/02; C07H 21/04

[52] U.S. Cl. .................... 435/6; 536/23.1; 536/24.3

[58] Field of Search ...................... 435/6; 536/24.3, 536/23.1

[56] References Cited

U.S. PATENT DOCUMENTS

| | | | |
|---|---|---|---|
| 4,925,785 | 3/1990 | Wang et al. | 435/6 |
| 5,124,246 | 6/1992 | Urdea et al. | 435/6 |
| 5,338,532 | 8/1994 | Tomalia et al. | 424/1.49 |
| 5,437,977 | 8/1995 | Seger | 435/6 |

OTHER PUBLICATIONS

Green, N. M., "Avidin and Strept avidin". In:Wilchek, M. & Bayer, E. A. ed., *Methods in Enzymology*, v. 184. San Diego:Academic Press. 1991 pp. 51–67.

Klevan et al., "Biotinylated Nucleotides for Labeling and Detecting DNA" In:Wilchek, M & Bayer, E. A., "Methods in Enzymology" v. 184, pp. 561–577, San Diego:Academic Press, 1991.

"Amplifying DNA Probe Signals: A Christmas Tree'Approach," *Bio/Technology*, vol. 6, pp. 1165–1168, Oct. 1998 Fahrlander et al.

"Affinity Capture Electrophoresis for Sequence-Specific DNA Purification," *GATA*, 9(3): 96–99, 1992, Ito et al.

"Sequence-specific DNA purification by triplex affinity capture," *Proc. Natl. Acad. Sci. USA*, vol. 89, pp. 495–498, Jan. 1992 Ito et al.

"Immuno-PCR with a Commercially Available Avidin System," *Science*, vol. 260, pp. 698–699, Apr. 1993 Ruzicka et al.

"Atomic force microscopy of biochemically tagged DNA," *Proc. Natl. Acid. Sci. USA*, pp. 3811–3814, May 1993 Murray et al.

*Primary Examiner*—George C. Elliott
*Assistant Examiner*—Scott David Priebe
*Attorney, Agent, or Firm*—Baker & Botts, L.L.P.; James Remenick

[57] ABSTRACT

The invention is directed to constructs and compositions containing multimeric forms of nucleic acid. Multimeric nucleic acids comprise single-stranded nucleic acids attached via biotin to streptavidin and bound with a functional group. These constructs can be utilized in vivo to treat or identify diseased tissue or cells. Repeated administrations of multimeric nucleic acid compositions produce a rapid and specific amplification of nucleic acid constructs and their attached functional groups. For treatment purposes, functional groups may be toxins, radioisotopes, genes or enzymes. Diagnostically, labeled multimeric constructs may be used to identify specific targets in vivo or in vitro. Multimeric nucleic acids may also be used in nanotechnology and to create self-assembling polymeric aggregates such as membranes of defined porosity, microcircuits and many other products.

16 Claims, 5 Drawing Sheets

ID

SEQUENCE LISTING ( 1 ) GENERAL INFORMATION:

( i i i ) NUMBER OF SEQUENCES: 2

( 2 ) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

ACCTGACAAG TCCTGGACAT                    20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

ATGTCCAGGA CTTGTCAGGT                    20

SELF-ASSEMBLING MULTIMERIC NUCLEIC ACID CONSTRUCTS

RIGHTS IN THE INVENTION

This invention was made with United States Government support under grant DE-FG02-93ER61656 awarded by the Department of Energy and the United States Government has certain rights in the invention.

BACKGROUND OF THE INVENTION

1. Field of the Invention

This invention relates to constructs, compositions and methods comprising multimeric forms of nucleic acid. One form of multimeric nucleic acid constructs comprise a streptavidin molecule bound with one or more single-stranded biotinylated nucleic acid molecules and an attached functional group. Constructs are used for the treatment or diagnosis of disorders both in vivo or in vitro, for the detection of target substances in samples and for construction purposes in nanotechnology and the creation of nucleic acid based polymeric aggregates.

2. Description of the Background

In recent years considerable interest has been generated in the use of anti-sense oligonucleotides and single-stranded DNA for in vivo therapeutic applications (G. Carter and N. R. Lemoine, Br. J. Cancer 67:869–76, 1993). Exciting examples include selective inhibition of viral DNA replication (C. K. Mirabelli et al., Anti-Cancer Drug Design 6:647–61, 1991) and gene expression (C. A. Stein and Y.-C. Cheng, Sci. 261:1004–11, 1993). The application of oligonucleotides into clinical medicine was encouraged by present advances with gene therapy such as the successful inhibition of viral gene expression in vivo by anti-sense DNA (M. Kulka et al., Antiviral Res. 20:115–30, 1991). Additional, in vivo applications have included oligonucleotide-antibody conjugates for tumor diagnosis and therapy (W. H. A. Kuijpers et al., Bioconjugate Chem. 4:94–102, 1993).

Others have investigated, in animal models, the pharmacokinetics, biodistribution and stability of an array of oligonucleotides ranging in size from 12 bases (T.-L. Chem et al., Drug Met. Disp. 18:815–18, 1990), to as large as 38 bases (J. G. Zendegui et al., Nuc. Acids Res. 20:307–14, 1992), and labeled with radioisotopes such as $^{125}$I (D. R. Elmaleh et al., J. Nucl. Med. 34:232P, 1993), $^{32}$p (A. S. Boutorine et al., Bioconjugate Chem. 1:350–56, 1990), $^{3}$H (T.-L. Chem et al., Drug Met. Disp. 18:815–18, 1990), $^{35}$S (S. Agrawal et al., Proc. Natl. Acad. Sci USA 88:7595–99, 1991), and $^{111}$In (M. K. Dewanjee et al., J. Nuc. Med. 34:174P, 1993). In these and other in vivo applications the nucleotide backbone was modified to stabilize the molecule against nuclease digestion, typically with methylphosphonates (D. M. Tidd and H. M. Warenius, Br. J. Cancer 60:343–50, 1989) or phosphorothioates (G. Goodarzi et al., Biopharm. Drug Disp. 13:221–227, 1992). Terminal modification alone was shown to provide sufficient stability in vivo (R. J. Boado and W. M. Partridge, Bioconjugate Chem. 3:5 19–23, 1992).

Amplification techniques for nucleic acids are under active investigation for in vitro applications. These include PCR (K. B. Mullis et al., Cold Spring Harbor Symp. Quant. Biol. 51:263–73, 1986), the "christmas tree" approach (P. D. Fahrlnder and A. Klausner, Bio/Technology 6:1165–68, 1988), and branching nucleic acid dendrimers (R. H. E. Hudson and M. J. Damha, J. Am. Chem. Soc. 89:585–91, 1993). Each of these methods rapidly amplifies nucleic acid molecules in vitro to a very great extent. However, using nucleic acids for amplification in vivo has not previously been considered.

SUMMARY OF THE INVENTION

The present invention overcomes the problems and disadvantages associated with current strategies and designs and provides constructs, compositions and methods for the treatment of disorders in humans, for the detection of disorders and other conditions in humans and in the environment, either in vivo and in vitro, and for the creation of polymeric assemblies of nucleic acid based monomeric constructs which may possess a wide variety of functional groups.

One embodiment of the invention is directed to constructs comprising a streptavidin molecule to which is bound a first biotinylated single-stranded nucleic acid, and a second biotinylated single-stranded nucleic acid. Attached to this multimer is a functional group forming a multimeric nucleic acid construct.

Another embodiment of the invention is directed to compositions containing multimeric nucleic acid constructs and a pharmaceutically acceptable carrier. Compositions can be used in the treatment or prevention of disorders in animals such as humans and may be administered systemically by injection or topically to form an aggregate at the site of a wound.

Another embodiment of the invention is directed to constructs comprising a coupling agent to which is bound two or more single-stranded nucleic acids with a functional group attached to the construct. Useful coupling agents include conjugated and multivalent linkers.

Another embodiment of the invention is directed to methods for treating a disorder comprising the steps of administering a biotin-conjugated antibody specific for the disorder and a multimeric nucleic acid construct to the patient. Constructs may contain functional groups such as toxins, isotopes, antibodies or pharmaceutically active components directed against the disorder.

Another embodiment of the invention is directed to a method for detecting a disorder in vivo comprising the steps of conjugating an antibody specific for the disorder with biotin and administering the conjugated antibody to the patient. A multimeric nucleic acid construct is prepared with a detectable label. Detectable labels include radioisotopes, chromatic chemicals, enzymes and metals. The labeled construct is administered and the location of the label determined to detect the presence or location of the disorder.

Another embodiment of the invention is directed to diagnostic aids and methods for using diagnostic aids for the in vitro detection of a target in a sample. Diagnostic aids comprise a biotin-conjugated antibody specific for the target and a multimeric nucleic acid construct containing a detectable label. Diagnostic methods comprise the addition of conjugated antibody and labeled constructs to the sample to detect the presence or location of the specified target.

Another embodiment of the invention is directed to nucleic acid-containing polymers formed from monomers comprising a streptavidin molecule bound to one or more single-stranded biotinylated nucleic acid. Nucleic acids may be bound with functional groups such as saccharides, lipids, fatty acids, nucleic acids, metals and amino acids. These polymers form products such as solids, liquids and gels.

Another embodiment of the invention is directed to methods for making nucleic acid-containing polymers formed from monomers of multimeric nucleic acid constructs. Polymers can be targeted with biotin-conjugated antibodies and formed in vivo or in vitro. These construct can also self-assemble to form useful products.

Other embodiments and advantages of the invention are set forth in part in the description which follows, and in part, will be obvious from this description, or may be learned from the practice of the invention.

DESCRIPTION OF THE INVENTION

As embodied and broadly described herein, the invention comprises constructs, compositions and methods for the non-enzymatic amplification of products at specific sites in vivo or in vitro. Antibody and oligonucleotide specificities are combined to greatly amplify the accumulation of functional moieties at the site or sites of a disorder in vivo, or the detection of a disorder or other contaminant in vivo or in vitro. Aggregates possessing an almost limitless amount of functional activity are assembled where needed and, at the same time, with minimal nonspecific accumulations in normal tissues. The diseased to normal tissue ratios of constructs is very high for both diagnostic and therapeutic applications. In addition, multimeric nucleic acid constructs can be used to create 3-dimensional assemblies of nucleic acid based polymers.

One embodiment of the invention is directed to a multimeric nucleic acid construct comprising a streptavidin molecule to which is bound a first biotinylated single-stranded nucleic acid and a second biotinylated single-stranded nucleic acid. This approach is based upon well investigated systems and has a number of advantages. Streptavidin has a high affinity for biotin. The nucleic acids, or species, are bound very strongly and specifically to the streptavidin molecule. The presence of nucleic acids allows for hybridization between complementary bases which further increases binding affinity and specificity between complementary nucleic acid sequences in natural settings. The assembled constructs, or aggregate, is quite efficiently and tightly bound together. Further, short nucleic acid molecules are non-toxic and can be radiolabeled relatively easily via a number of strategies.

Attached to the streptavidin/biotin linked nucleic acid multimer may be a functional group. Functional groups are those portions of the construct which provide functional or structural activity directed toward the specific use of the construct. Examples of functional groups include radioisotopes, toxins, cytokines, pharmaceutically active moieties or components, proteins, metals, metabolic analogs, genes, antigens, enzymes, antibodies and antibody fragments, nucleic acids, oxidizing agents, bacteriostatic and bacteriocidal agents, or combinations or parts thereof. Attachment may be non-covalent such as by electrostatic, hydrophobic or hydrophilic interactions, or by covalent binding. Techniques for attaching functional groups to the multimer are particular to the group being attached and may be direct or indirect. For example, direct attachment may be by covalent modification of the functional group, the nucleic acids or both, such as by conjugation. Indirect attachment may be by modification of the functional group, the nucleic acids or both with another substance such as *E. coli* or other single-stranded or double-stranded binding proteins such as Rec A proteins, T4 gene 32 proteins or major or minor groove nucleic acid binding proteins, and G protein complexes. Coupling agents which facilitate attachment include avidin/biotin, streptavidin/biotin, receptor-ligand interactions, antibody/antigen pairs, Staphylococcus aureus protein A/IgG antibody Fc fragment, and chimeras including streptavidin/protein A chimeras. There are also many different chemical coupling agents such as streptavidin, avidin, SMCC (succinimidyl 4-(N-Maleinideomethyl)cyclohexane-1-carboxylate. 5'-amino-containing oligonucleotides, 5'-thiol-containing oligonucleotides and polyamidoamines.

Alternatively, a part or portion of the nucleic acid species may itself be the functional group. For example, certain nucleotide sequences are known binding sites for specific proteins. A nucleic sequence can be engineered into the species to be bound to streptavidin and the resulting construct utilized. After assembly of the aggregate of constructs, the binding protein, which may be modified with another constituent (creating a chimeric or fusion protein product), is added to the assembly. In this manner, formation of the assembly can precede treatment. In addition, it is also possible to remove the old constituent and substitute new constituents without disassembling the aggregate. Aggregates should be useful for many such substitutions. Further, because the aggregate is a biological substance, it is not expected to be harmful to a patient when used in, for example, therapeutic procedures. The aggregate is expected to persist in the patient's body for a sufficient period of time, possible days, weeks, months or longer, to complete a full course for most types of therapy.

Nucleic acid species may comprise DNA, RNA or PNA, (polyamide nucleic Acid) although it may be possible to substitute short sequences of amino acids for the nucleic acid. The nudeic acid is typically about 5, 10, 15, 20, 25, 30, 35, 40, 45 or 50 nucleotides in length, and preferably between about 8 to about 23 nucleotides in length. Longer sequences are generally not preferred because the larger the nucleic acid, the more cumbersome to use and the more difficult it would be for such constructs to pass through small spaces such as biological or synthetic membranes or tissues. When transport through a porous object is not necessary, larger nucleic acid species may be used.

The streptavidin molecule may be bound with one, two, three or more nucleic acid species. Three is preferred to provide the maximum number of functional groups or supporting structures while still providing a free biotin binding site on the streptavidin molecule for further binding which may also be to a functional group. Starburst arrangements are also possible with multivalent linkers which radiate 4, 5, 6, 8, 10, 12 or more single-strand species. These starburst dendrimers are constructed using a divalent linker such as SMCC (succinimidyl 4-(N-maleimidomethyl) cyclohexane-1-carboxylate) and a derivatized amino- or thiol-containing compound such as reduced S-pyridylcysteamine modified oligonucleotide. These linkers have 6–12 available amines for binding nucleic acids. Other similar approaches may be used which start with easily prepared 5'-amino- or 5'-thiol-containing oligonucleotides.

Nucleic acids may be made synthetically, recombinantly or isolated from biological sources using techniques known to those of ordinary skill. Nucleic acids covalently attached to biotin may be purchased commercially or may be created through recombinant or biochemical techniques. Biotin can be obtained commercially or purified as the water-soluble vitamin. Streptavidin is a protein composed of four identical subunits with an approximate molecular weight of 60,000 daltons and can be purchased commercially or purified from *Streptomyces avidinii* (N. M. Green, Biochem. J. 89:585–89, 1963). Streptavidin is preferred, but avidin may also be utilized in these constructs with nearly equal efficiency.

The sequence of each of the nucleic add species, including the first, second, third or more species, may be the same or different, may comprise a small or large number of complementary sequences, may have a defined sequence or may have entirely random sequences. One feature of non-identical sequence constructs is that when used for the treatment of patients, multiple treatments can be administered, repeatedly exposing the patient to the same collection of nucleic acids without the risk of an adverse immune response to the sequence. If necessary, a sequence can be chosen that is unique and not present anywhere in the patient's genome. Biological side reactions from the added nucleic acid sequences would not be expected to occur. Nucleic acids utilized may be complementary providing a further binding function to each construct. Complementary constructs can be used sequentially to maximize accumulation at a target site. Cycles of complementary constructs can be administered to create the aggregate in stages. In this manner, it is also possible to create a layered aggregate using complementary construct with distinct functional groups.

Another embodiment of the invention is directed to compositions comprising multimeric nucleic acid constructs plus a pharmaceutically acceptable carrier such as water, saline, alcohol, polyethylene glycol, oil, polysaccharides, salts, glycerol, stabilizers, anti-oxidants, emulsifiers and combinations thereof. The function of the carrier is to provide a suitable medium for introduction of the construct in or on the patient's body. When compositions are used internally, carriers of saline, buffer and salts maybe useful. When used externally, carriers such as water, oils and alcohols may be useful. Compositions may further comprise other ingredients such as anti-oxidants to prevent oxidation of constructs, anti-bacterial or anti-viral agents to reduce contamination, or other chemotherapeutic agents to treat the disorder.

Another embodiment of the invention is directed to a general class of multimerle constructs comprising a coupling agent to which is attached two or more single-stranded nucleic acids. Coupling agents are chemicals which allow for the attachment of multiple species of nucleic acid. Some of the more useful agents include streptavidin, avidin, succinimidyl 4-(N-maleimidomethyl)cyclohexane-1-carboxylate (SCMM), 5'-amino-containing oligonucleotides, 5'-thiol-containing oligonucleotides and polyamidoamines. These chemicals can be used to create multimeric nucleic add constructs containing 2, 3, 4, 5, 6, 7 and more species of nucleic acids per molecule. The resulting aggregates will have multiple points of interaction. The constructs may further contain the same functional groups as described above and those functional groups may be the nucleic acids themselves.

Another embodiment of the invention is directed to a method for treating a disorder in a patient comprising the steps of administering an antibody, conjugated with biotin, specific for the disorder, and a multimeric nucleic acid construct to the patient. Attached to the constructs are one or more functional groups to treat or prevent the specific disorder. Functional groups may be added before or after creation of the resulting aggregate of constructs. Functional groups may be attached to the streptavidin coupling agent or to one or more of the nucleic acids. Multiple functional groups can be attached to a single construct and, if desired, constructs can be entirely saturated.

Methods for the production of antigen-specific antibodies are disclosed in *Current Protocols in Immunology* (J. E. Coligan et al., editors; John Wiley and Sons; New York, N.Y., 1991), and *Antibodies: A Laboratory Manual* (E. Harlow and D. Lane, editors; Cold Spring Harbor Press; Cold Spring Harbor, N.Y., 1988), which are hereby specifically incorporated by reference. Antibodies may be of the class IgG, IgM, IgA, IgE, IgD and parts and combinations thereof, and may be monoclonal or polyclonal, or comprise fragments of antibodies such as Fab fragments or Fv fragments. Biotin conjugated antibodies may be obtained commercially or prepared from purified biotin and the desired antibodies. Techniques for the coupling of biotin to antibodies are disclosed in *Immunochemical Protocols* (Methods in Molecular Biology, Vol. 10; M. M. Manson, editor; Humana Press; Totowa, N.J., 1992), which is hereby specifically incorporated by reference.

Nucleic acid constructs may comprise one, two or three species of single-stranded nucleic acids bound to streptavidin or comprise dendritic nucleic acid starbursts. These nucleic acids may be the same or different may comprise complementary sets of sequences. The nucleic acids may comprise a double-stranded portion when, for example, a particular structure is desired of the assembled network of constructs or to facilitate coupling of one or more functional groups. In addition, specific nucleotide sequences may be engineered into one or more of the nucleic acid species to attract a particular pharmaceutically active component to the site of aggregate formation after formation has been completed. Multiple different sequences can be introduced to allow for the administration of different pharmaceutical components.

Functional groups which may be useful for the treatment of disorders in a patient include radioisotopes, toxins, cytokines, pharmaceutically active moieties, proteins, metals, metabolic analogs, genes, antigens, enzymes, antibodies and antibody fragments, nucleic acids, oxidizing agents, bacteriostatic and bacteriocidal agents, and combinations and parts thereof. For example, radioisotopes are useful against certain neoplasias. Toxins, such as animal toxins, plant toxins, bacterial toxins, fungal toxins, viral toxins and parasitic toxins, are useful against specific infections. Preferred toxins include *Pseudomonas* toxins, *Diphtheria* toxins, *Escherichia* toxins and ricin. Cytokines are useful when targeted to certain cells or tissues to elicit a desired function attributed to that cytokine. Useful cytokines include T cell growth factors, B cell growth factors, granulocyte/macrophage growth factors, granulocyte growth factor, macrophage growth factor, stem cell growth factor, transforming growth factor, erythropoietin, bone morphogenic proteins, differentiating agents, interleukins, interferons, hormones, components of the complement system and combinations thereof. Particular antigens may also be useful when targeted to diseased cells or tissues to induce or bolster an immune response. Functional groups Which are proteins may be coupled to other proteins either covalently, such as fusion proteins or chimeric proteins, or non-covalently such as electrostatically. These other proteins may be proteins which recognize and bind to specific sequences present only on the nucleic acid species of the constructs. In this way, pharmaceuticals can be delivered to multiple sites within a patient simultaneously and with a great deal of specificity and accuracy.

Disorders in which constructs and compositions may be used for therapeutic or prophylactic purposes including diseases, infections, neoplasias and genetic defects and deficiencies. Neoplasias treatable in this manner include leukemias, lymphomas, sarcomas, carcinomas, neural cell tumors, squamous cell carcinomas, germ cell tumors, metastases, undifferentiated tumors, seminomas, melanomas, neuroblastomas, mixed cell tumors, neoplasias caused by infectious agents and other malignancies. Treatable infections include infections caused by bacteria, viruses and parasites, and also fungal infections such as yeast and deep fungal infections which are difficult to treat conventionally.

Preferably, complementary sets of nucleic acid constructs are prepared and sequentially administered. For example, a first set of identical constructs are administered and allowed to assemble. Next, a second set of complementary constructs are administered which bind and hybridize to the first set. This pattern or cycle is repeated as desired allowing the resulting assembly to build exponentially to a predetermined and possibly very large size. Alternatively, both sets of complementary construct may be mixed simultaneously provided the assembly has time to form. Assembly times are dependant upon the size of the individual constructs and the size of the assembly desired. Relatively short incubation periods are expected, on the order of minutes, due to the rapid binding of biotin to streptavidin and rapid hybridization of complementary nucleic acids. Further, aggregates can be constructed at multiple sites even when those sites have not been previously identified. Defined structures can be created at specific sites and the activity of the functional groups attached to each construct will be concentrated at these sites, such as radioactivity at tumor sites or sites of metastatic spread of diseased cells.

Treatments may be administered topically to treat or prevent diseases and infections on the exterior of the patient, or administered parenterally, sublingually, rectally or enterally, to treat or prevent systemic disorders. Patients which may be treated with these methods include animals and preferably humans. Treatments, such as the treatment of neoplasias, may be supplemented with one or more chemotherapeutic agents such as alkylating agents, purines and pyrimidine analogs, vinca and vinca-like alkaloids, etoposides and etoposide-like drugs, antibiotics, corticosteroids, nitrosoureas, antimetabolites, platinum based cytotoxic drugs, hormonal antagonists, anti-androgens and anti-estrogens. Treatments may also be supplemented with other therapies such as radiation therapy or immune therapy to further attack the disorder.

Another embodiment of the invention is directed to methods for detecting a disorder in a patient in vivo. Antibody, which may be polyclonal or monoclonal, as described above, is conjugated with biotin and administered to the patient. A multimeric nucleic acid construct comprising one or more biotinylated single-stranded nucleic acids bound to streptavidin is labeled with a detectable label. Useful labels include radioisotopes, stable isotopes, enzymes, fluorescent and luminescent chemicals, chromatic chemicals, metals and electrical charges. The labeled constructs are administered to the patient and their location determined by autoradiography, nuclear magnetic resonance (NMR), magnetic resonance imaging (MRI), or other means suitable for the label. Disorders which can be detected include diseases, infections, neoplasias and genetic defects and deficiencies. Diagnosis of the particular disorder may be for precise targeting of other therapeutic procedures such as surgical or radiotherapy, or as a means for determining the presence or severity of the disorder.

Another embodiment of the invention is directed to in vitro diagnostic aids and methods for the in vitro detection of a target in a sample. The diagnostic aid comprises a biotinylated antibody specific for the target and a multimeric nucleic acid construct labeled with a detectable label. The biotin-conjugated antibody may be polyclonal or monoclonal or antibody fragments such as Fab or Fv fragments. Constructs may comprise one, two, three or more nucleic acid species attached to the streptavidin molecule. Nucleotide sequences may be the same or different, and preferably, the constructs are prepared in complementary sets to be administered sequentially. The detectable label may be a radioisotope, stable isotope, enzyme, fluorescent or luminescent chemical, chromatic chemical, metal or electrical charge. Each of these labels can be detected through various means known to those of ordinary skill such as by autoradiography, NMR, MRI and other suitable detection means.

The target may be a protein, nucleic acid, metal, cytokine, viral or bacterial component, immunoglobulin, enzyme or a part or combination thereof. Targets may also be contaminants in the environment or other harmful substances that are suspected of having accumulated in the patient. The are virtually no limits to the types of targets which can be detected provided that they can be identified antigenically or by hybridization kinetics. Because accumulation of construct at target site is exponential, targets undetectable by other means including polymerase chain reaction (PCR), can be detected with multimeric constructs and in many instances, immediately detected visually, a significant advantage over current methodologies including PCR procedures.

Many different types of sample suspected of containing the target substance may be tested. The only limiting condition is that the multimerle acid nucleic acid construct be able to diffuse throughout the sample to selectively assemble at specific sites. Useful samples may be obtained from biological sources, the environment, and even samples from manufacturing techniques and processes where it is desirable to know whether a specific target is present. Diagnostic aids may further comprise an agent such as water, saline, alcohol, polyethylene glycol, oil, polysaccharides, salts, glycerol, anti-oxidants, emulsifiers and combinations thereof to increase the shelf-life or stability of the components, or to facilitate use.

Another embodiment of the invention is directed to in vitro methods for detecting a target in a sample. For example, one method comprises the steps of conjugating an antibody specific for the target with biotin and adding the conjugated antibody to the sample. A multimeric nucleic acid construct is prepared comprising one or more biotinylated single-stranded nucleic acids bound to streptavidin. The construct is labeled with a detectable label and the labeled construct added to the sample. Examples of detectable labels include radioisotopes, stable isotopes, enzymes, fluorescent and luminescent chemicals, chromatic chemicals, metals and electrical charges.

Labeled constructs may be added once or many times to facilitate accumulation of label at the target site and subsequent detection of the target. Targets which can be detected include proteins, nucleic acids, metals, cytokines, viral and bacterial components, immunoglobulins, enzymes and parts and combinations thereof. Labeled constructs may be detected and localized in the sample using, for example, autoradiography, visual detectors, fluorescent detectors, radioactivity detectors, chromatic detectors, electrical detectors and any other means suitable for the particular label chosen.

When testing biological samples for target substances, the presence or absence of target may be indicative of a disorder. Samples for testing may be obtained from tissues, cells, blood, urine, cerebrospinal fluid, lymph and amniotic specimens. For example, amniotic cells can be tested for genetic disorders. Numerous cancers can be confirmed by the presence of tumor-associated antigens in samples of blood or urine. The presence of a viral infection can be confirmed by the presence of viral specific antibodies or sometimes antigen in a sample of the patient's serum. Disorders which can be detected by this method include diseases, infections, neoplasias and genetic defects and deficiencies. Samples from environmental sources, such as lakes, streams, rivers, land-fills, marshes and just plain earth, may be used to detect certain contaminants such as metals, pesticides, microorganisms or toxic wastes. Samples obtained from manufacturing processes of raw materials, intermediate or finished product may be tested for the presence or absence of certain targets including contaminants. Alternatively, sample may be tested to determine the concentration of various ingredients in the finished product as a means for quality control.

Another embodiment of the invention is directed to nucleic acid-containing polymers formed from monomers comprising a streptavidin molecule bound to one or more biotinylated single-stranded nucleic acids. Functional groups may be attached to the monomers at the streptavidin molecule or the nucleic acid, may be a portion of the nucleic acids themselves, or may be added after assembly of the polymer. Polymers may comprise monomers which are the same or different and may be a solid, a liquid or a gel. Useful solids include membranes, plastics, coatings, resins and other materials of defined porosity including chromatography reagents (which may also be a gel), pharmaceuticals, and nearly any substance with can be assembled from monomers. Useful liquids include polymeric substances such as plastics and coatings which may be paints, dyes, metals and other inorganic and organic compounds. Polymers can also be utilize in nanotechnology in the design and construction of microcircuits and electronic switches, in manufacturing of continuous protein fibers such as silk, and in the production of multi-layered micro-components.

Because the base monomer comprises mostly nucleic acid, it may be desirable to eliminate that nucleic acid after the aggregate has assembled. This can be easily accomplished with enzymes such as specific or nonspecific nucleases or alkali treatments to the aggregate.

Another embodiment of the invention is directed to a method for making a nucleic acid-containing polymer comprising the steps of creating a monomer comprised of a streptavidin molecule attached to one or more biotinylated single-stranded nucleic adds, and polymerizing the monomers. The monomer may further comprise an attached functional group such as an isotope, a saccharide or an animo acid, or the nucleic acid sequence may be engineered to have a specific sequence. A number of monomers are then combined to create the polymer which may be a solid, a liquid or a gel. The number of monomers which can be combined to create the polymer may be very large or relatively small, and will mostly depend upon the space available for formation of the polymer or the amount of functional activity desired. The functional group may be a saccharide, lipid, fatty acid, nucleic acid, metal, amino acid and modifications and combinations thereof. Functional groups may be major or minor components of the resulting polymeric assembly. Polymers may comprise identical or different monomers in random or defined patterns such as in layers of different altering monomers. Antibodies including biotin-conjugated antibodies can be added to the polymerization to specifically direct polymerization to predetermined or specific sites both in vivo and in vitro.

The following examples illustrate embodiments of the invention, but should not be viewed as limiting the scope of the invention.

EXAMPLES

Example 1 Nucleic Acid Amplification Schemes in vitro and in vivo.

Figure 1A:
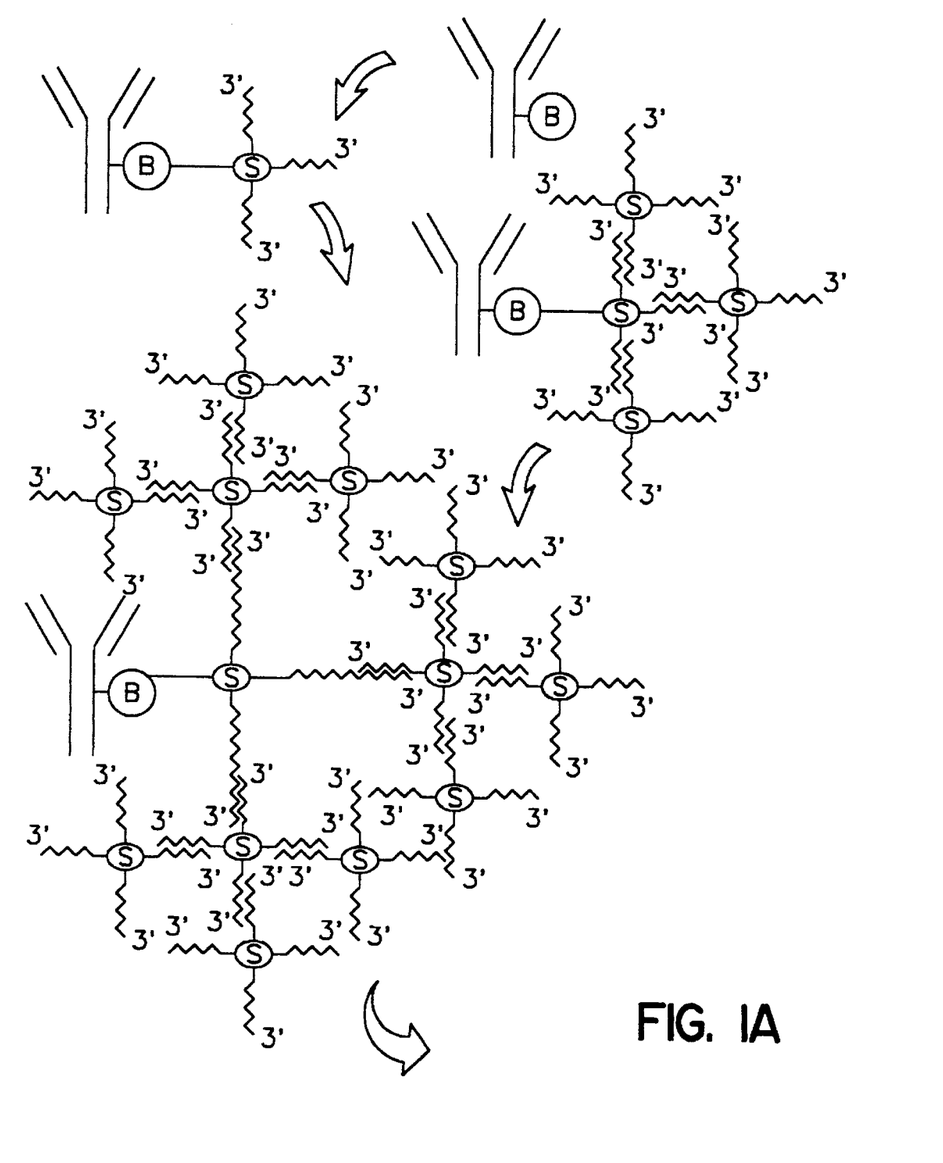
FIG. 1 Constructs of a protein-nucleic acid aggregate using a biotinylated anti-breast tumor antibody and streptavidin containing single-stranded DNA molecules.
Figure 1B:
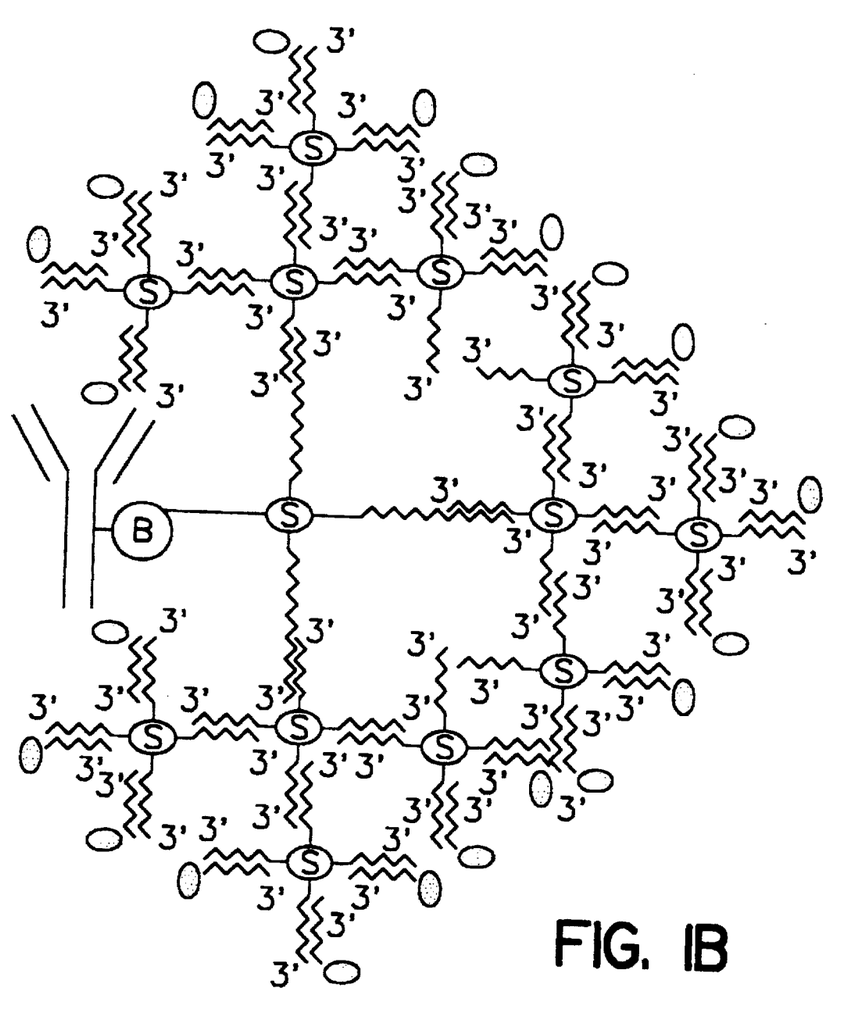

Nucleic acid amplification schemes, both in vitro and in vivo, are tested in a mouse model with breast tumor xenograft for the ability to construct nucleic acid aggregates containing high quantities of radiolabel restricted essentially to the tumor. Two novel amplification strategies include a protein-nucleic acid aggregate and a pure nucleic acid aggregate. The construction of a protein-nucleic acid aggregate using a biotinylated anti-breast tumor antibody and streptavidin containing a single-stranded molecule are shown in FIG. 1.

This anti-breast tumor antibody conjugated with biotin is administered to a mouse model with a breast tumor xenograft. (A direct DNA-conjugated antibody could also be used.) This is followed by the administration of a streptavidin conjugate containing three identical biotinylated single-stranded DNA molecules, each 20 to 24 bases in length. This construct preserves one of the 4 biotin sites on streptavidin for binding to the biotinylated antibody located at the tumor. Next, a similar streptavidin complex is administered containing four single-stranded DNA molecules complementary to the first. By alternating the injections among pairs of complementary oligonucleotides, an aggregate is built at the tumor site. Finally, the radiolabel is administered as the final injection and in the form of a radiolabeled single-stranded DNA.

The intermediate injections consist of streptavidin with three or four single-stranded DNA molecules. These complexes were selected for the ease in preparing a molecule with multiple, spatially-separated oligonucleotides. Streptavidin has four high affinity binding sites for biotin (Kd of $10^{-15}$M). Also, end-biotinylated single-stranded DNA molecules are easily bound to streptavidin. Optionally, endogenous biotin may be removed from the streptavidin-DNA amplification system, if necessary, by HPLC, FPLC, chromatography or other separation technique to avoid any interference that might occur. Adding the appropriate molar ratios, streptavidin-DNA complexes containing four oligonucleotides are obtained. A complex with three oligonucleotides and a vacant binding site is made by absorbing streptavidin on beads derivatized with 2-iminobiotin. This analog of biotin is released from the binding site under conditions where biotin remains bound. The steric constraints of binding to beads ensures that only a single binding site of the protein is used. Next, biotin-labeled oligonucleotides are saturated to the other binding sites and the complex is removed from the beads by treatment at slightly acidic pH. If necessary, the resulting complex can be purified from any contaminating species by gel electrophoresis or HPLC procedures.

Biotinylated oligonucleotides, when bound to avidin (a protein with nearly identical biotin-binding properties and 3-dimensional structure as streptavidin), are protected in vivo against nuclease digestion. Therefore, it is not necessary to modify the oligonucleotides to protect from in vivo enzymatic digestion. This has the additional advantage of eliminating concerns of diminished stability of DNA duplexes with two chemically modified strands.

Streptavidin is a 60 KDa protein which, with four 20-base strands DNA, will have a molecular mass of 86 kDa. Radiolabel is attached to this complex at the last step of the amplification as single-stranded 20-base strands with molecular masses of only 6.6 KDa. Ultimately, it may be more attractive to replace the streptavidin with a smaller polyvalent carrier from which will radiate the multiple single-stranded DNAs. A smaller size complex will show improved diffusion, for example, into a tumor. The use of such DNA complexes also eliminates the possibility of an immune response against streptavidin.

Example 2 Dendrimeric Nucleic Acid Complexes.

Figure 2:
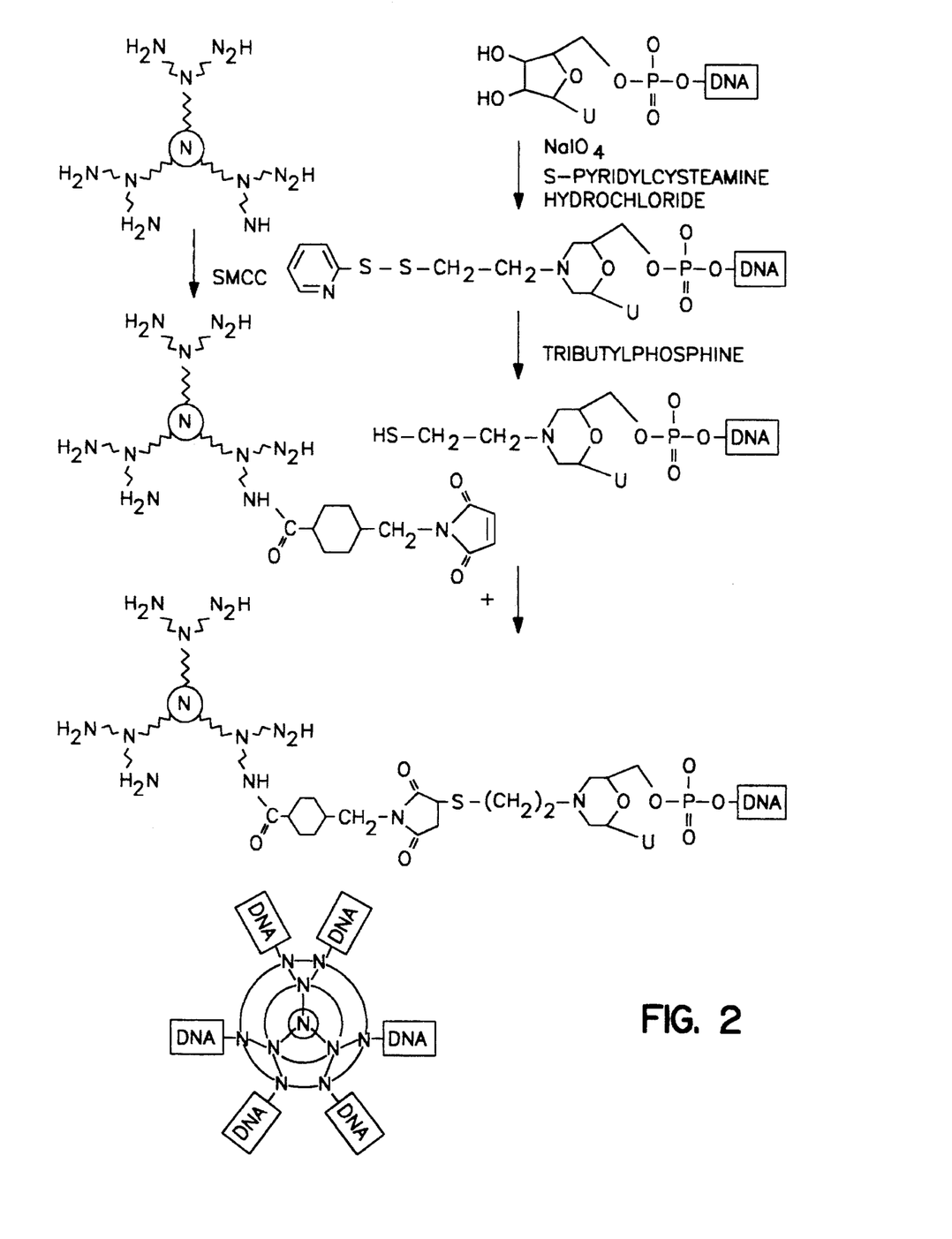
FIG. 2 Process for the conjugation of DNA, containing a thiol protected uracil, to a polyamine dendrimer derivatized with multiple maleimide groups and a schematic of the expected product.

A complex containing a central core from which radiates 4–6 DNA singlestrands (20-mer in length) is constructed using a starburst dendrimer as described by Tomalia (D. Tomalia, New Scientist, November, pp.30–34, 1991). Complexes are grown from linear components using integral nucleic acids as branching points. The nucleic acid dendrimer is constructed based on the shell-like core of the multiple-generation dendrimer developed by Tomalia (starburst dendrimer based on polyamidoamines, PAMAM). In this manner a sphere containing a layer of repetitive functional sites is easily constructed with the size of the unit and number of functional groups dictated by the choice of repeating units. FIG. 2 shows the dendrimer used and the chemistry of oligonucleotide attachment. DNA singlestrands are attached to the 6–12 available amines using the multivalent linker SMCC (succinimidyl 4-(N-maleimidomethyl) cyclohexane-1-carboxylate) and a reduced S-pyridylcysteamine modified oligonucleotide. (Other similar approaches may be used which start with easily prepared 5'-amino- or thiol-containing oligonucleotides.) Using PAMAM as a core, a molecule containing up to six 20-base oligonucleotides is constructed. The estimated molecular mass of the dendrimer with six 20-base oligonucleotides bound is about 40 kDa.

Other possible nucleic acid complexes include synthetic holiday junctions with pendant single stranded ends. These compounds are easily made and smaller than the streptavidin oligonucleotide construct and should be useful as constructs.

Figure 3:
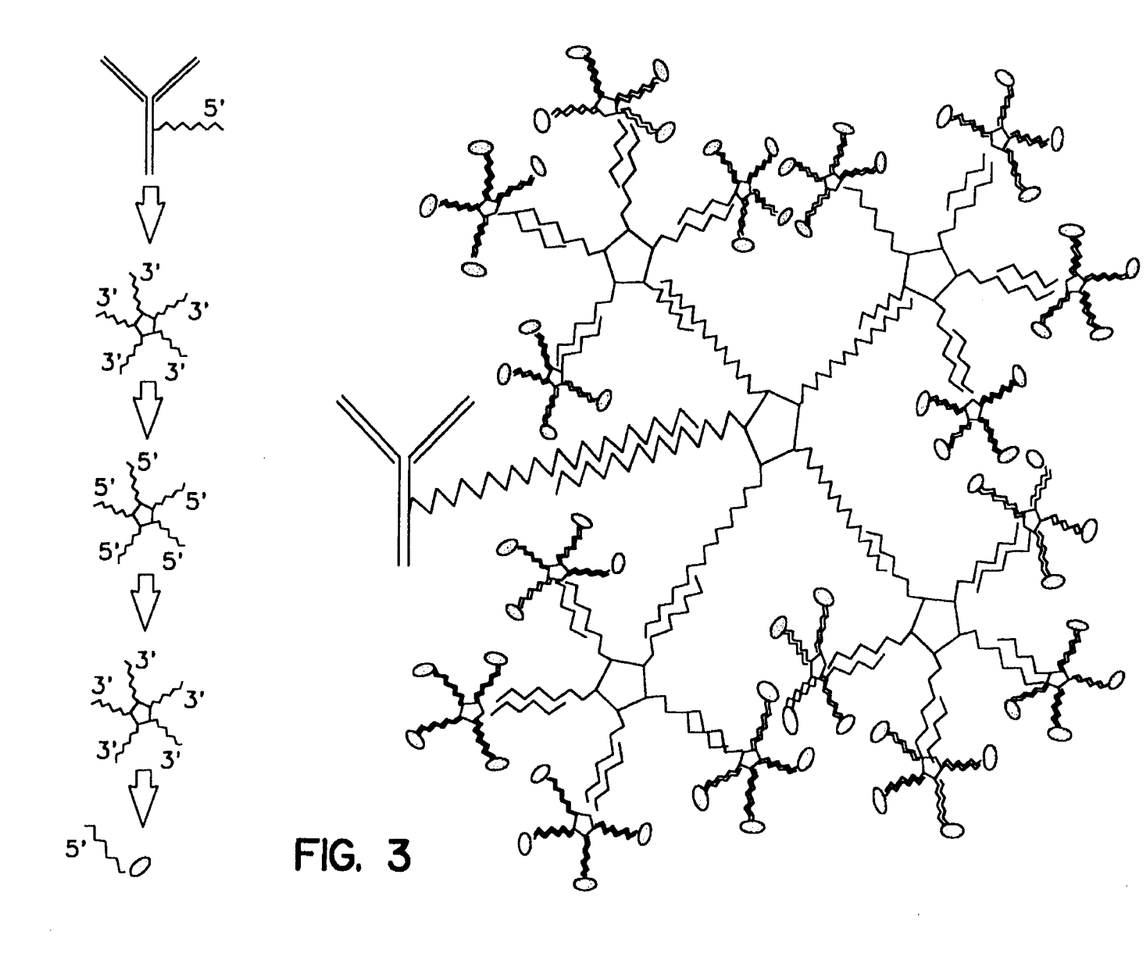
FIG. 3 Construction of a nucleic acid aggregate using an anti-breast tumor antibody containing a single-stranded DNA with dendfimeric nucleic acid complexes.

The first injection consists of an anti-tumor antibody conjugated with a single 20-mer oligonucleotide (FIG. 3). Subsequent administrations consist of the oligonucleotide complexes described above, and followed by a second oligonucleotide complex containing complementary strands. The smaller size of these species compared with the streptavidin complex makes it possible to administer the radiolabel as part of these DNA complexes with each administration while maintaining favorable tumor to background ratios. In the more conservative approach illustrated in FIG. 3, the radiolabel is administered in the final injection on a single-stranded DNA.

The successive addition of complexes containing multiple single-stranded DNAs leads to the formation of a large aggregate. Each cycle of addition of complementary DNA strands, for tetra-valent reagents, results in up to a three-fold increase in the number of strands added to the aggregates. This amplification is greater than that of PCR. Using these methods it is possible to construct an aggregate at each antigenic site, which contains an exponential increase in the amount of radiolabel achievable by direct labeling techniques. Moreover, the radioactivity is concentrated at the tumor due to the quick clearance of the low molecular weight-radiolabeled strands from circulation and from normal tissues.

Example 3 Tumor Model and Antibodies.

One difficulty in breast cancer research is that only a few human cell lines are available for experimentation in vitro, and even fewer are continuously transplantable with sustained and vigorous growth. In contrast, tumors of breast cancer patients can have different growth rates, be diploid or aneuploid and express different levels of breast epithelial antigens, with each characteristic usually varying independently. Recently, investigators have been able to develop and characterize 12 breast tumor cell lines transplantable in Balb/c nu/nu nude mice. These cell lines exhibit a range of diverse tumor characteristics such as ploidy, percent S phase, and epithelial mucin, expression by immunohistochemistry and flow cytometry. The authors conclude that the low transplantable human breast tumors represent a diversity found in breast cancer patient populations and that they could be used as a desirable and comparable experimental mode in breast cancer studies.

In addition, a number of antibodies directed against the human milk fat globule, mucin were developed. Two of these, the Mc5 and BrE3 recognize distinct epitopes of human breast mucin and, together, allow each of the 12 tumor types described above to be distinguished by immunocytogenetics. Furthermore, it is likely that neither antibody will be rapidly internalized by breast cancer cells (although there is indirect evidence the BrE3 may show some internalization in small-cell lung cancer lines). Therefore, these antibody-tumor combinations are ideal for use in these experiments. The tumor cell line, designated ZR-75-1 is both ER+, scores highly in binding studies with both the Mc5 and BrE3 antibodies and is a fast grower making it a good candidate for this approach.

Example 4 Preparation of Derivatized Antibodies.

Anti-breast tumor antibodies (IgG) can be biotinylated with approximately one biotin per molecule using NHS-X biotin (Calbiochem, San Diego, Calif.). These antibodies are covalently conjugated with a 20-mer single-stranded oligonucleotide using SMCC as a cross-linking agent (Pierce Chemical; Rockford, Ill.). A ratio is chosen to yield an antibody to oligonucleotide molar ratio of 1 with the efficiency of conjugation determined by gel electrophoresis with and without the addition of labeled complementary probes. Alternatively, the antibodies can be conjugated to DNA using Fab' fragments conjugated to single-stranded oligonucleotides via disulfide bonds.

Example 5 Oligonucleotide Preparation.

Oligonucleotides are obtained commercially or synthesized with an automated DNA synthesizer (Operon Technologies, Alameda, Calif.) or an EMBL multiplex oligonucleotide synthesizer which allows the simultaneous preparation of ten 20-base oligonucleotides. Where needed, biotin is added at the 5'-position by the use of biotin phosporoamidite.

Previous studies involving oligonucleotides in vivo have shown that, when not conjugated with avidin, modification of the DNA is necessary to enhance its stability. Minimal modification, such as the addition of a 3'-amino group, is typically sufficient to enhance in vivo stability. The oligonucleotide modifications are: biotinylation; diethylenetriaminepentaacetic acid (DTPA) chelation; and attachment to a central core; may be enough to retard nuclease digestion. If necessary, oligonucleotides can be modified further to enhance stability in vivo. Additional modifications that can be used were procedures described previously, and further, single or double strand substitutions with polyamide nucleic acid (PNA; a peptide nudeic acid), nucleic acid analogues or single-stranded DNAs complexed with polyvalent cations can further enhance in vivo stability.

Example 6 Choice of DNA Sequences.

Since DNA amplification schemes are carried out non-enzymatically, a wide range of temperature and environmental conditions are used. However, for in vivo amplification, physiological salt and 37° C. is used. The major variable that can be adjusted to assist efficient amplification is the base composition of the DNA. Higher A+T contents will allow for lower annealing temperatures. Usually optimal annealing occurs at around 15 to 20 degrees below the melting temperature, but this is highly dependent on the extent to which the separated strands can form stable hairpins. DNA sequences that have no obvious ability to form hairpins are chosen. Such a pair of sequences with 50% A+T are 5'-ACCTGACAAGTCCTGGACAT-3' (SEQ ID NO 1) and its complement 5'-ATGTCCAGGACTFGTCAGGT-3' (SEQ ID NO 2). With such sequences, almost any base composition should show rapid and efficient annealing. However, several different 20-base sequences, representing a range of base compositions are tested. If sequence does affect the amplification efficiency, it is relatively easy to choose sequences that maximize the amplification yield.

Example 7 Radiolabeling of Oligonucleotides.

Oligonucleotides are radiolabeled with indium-111 ($^{111}$In), a radionuclide with a convenient 67-hour physical half-life commonly used for imaging applications. This radionuclide is often attached to carrier molecules by chelation to DTPA previously conjugated to the carrier. In this form, rain has been shown to be stably bound in vivo. Also, DTPA has been described in the radiolabeling of an animohexyloligonucleotide with $^{111}$In for animal imaging studies.

Oligonucleotides are conjugated with DTPA by first introducing an alkylamino group by condensation with aminopropanol and, after deprotection, acylated with the dianhydride of DTPA as described for DTPA. Thereafter, the conjugated oligonucleotides is radiolabeled by chelation with rain using standard methods.

Example 8 In Vitro Testing.

Antibody functionality: Mild modification, such as one biotin per antibody molecule, has minimal effects on immunoreactivity. To confirm this, the biotinylated anti-breast tumor antibody and the antibody-oligonucleotide conjugate are tested for immunoreactivity using a competition binding assay.

Streptavidin functionality: The biotinylated antibody (radiolabeled with $^{111}$In via DTPA conjugation) is tested for its ability to bind to streptavidin-conjugated polystyrene beads and the antigen. The percentage of labeled antibody bound when beads are incubated with varying antibody concentrations indicates the percentage of reactive molecules. Similarly, the ability of streptavidin to bind four 20-base oligonucleotides is tested by electrophoretic analysis of the complexes formed. The streptavidin-oligonucleotide complex are then be tested for binding to the biotinylated and antibody again using gel electrophoresis and/or HPLC.

DNA duplex formation: The antibody conjugated to the 20-base oligonucleotide is tested for its ability to anneal with its complementary 20-base strand. Comparisons are made in buffer, culture media and human serum (at 37° C.) using the complementary single-stranded oligonucleotides. Results are evaluated by gel electrophoresis and size exclusion HPLC. Similarly, the ability of a streptavidin-DNA complex to anneal with complementary DNA strands is tested in buffer and in serum, by separating the complexes formed using gel electrophoresis, with radiolabeled strands used, where necessary to prove the stoichiometry of particular species.

Stability of the dendrimeric complex: The dendrimeric oligonucleotide complex is tested in serum for stability against nucleases. Changes in gel electrophoretic patterns indicates if digestion occurred. Additionally, the binding of the complementary strand (before and after addition to serum) and its gel analysis indicates the ability of this dendrimeric DNA complex to bind to its complementary DNA strands as well as if enzymatic digestion has occurred. Radiolabel bound to DNA single-strands is tested for stability in serum at 37° C. through 48 hours at concentrations expected to be experienced in patients (approximately 1 mg/ml serum). Parallel experiments are carried out with double-stranded complexes. Periodically, samples are removed for analysis by size exclusion HPLC and gel electrophoresis.

Amplification efficiency: The concept of aggregate formation is tested in vitro by a number of methods. Biotin-conjugated polystyrene beads are first used to represent biotinylated antibody bound to tumor cells. The binding of the streptavidin-DNA complex and subsequent aggregate formation with the complementary complex (as defined in FIG. 1) is followed with $^{111}$In-labeled oligonucleotides. Next, antibody coated beads are tested with both the biotinylated antibody and the antibodyoligonucleotide complex in separate studies. Third, an approach most closely simulating the in vivo application, direct targeting and amplification of DNA is used to label antigen or monolayer cultures of tumor cells. To demonstrate amplification, a multiplicative effect of added radiolabel is demonstrated with each subsequent addition. The results are monitored by autoradiography.

Multiple simultaneous amplification reactions: Since the DNA sequences used for amplification are arbitrary, two or more different amplification reactions can be carried out simultaneously, without cross interference, by choosing sequences that cannot cross-hybridize to any significant extent. In principle, this allows multiple antigens to be tested in the same mouse, simultaneously, or controls with unlabeled antibodies to be carried out simultaneously with tests using labeled antibodies. It may be necessary to use two distinguishable radioisotopes on distinct DNA sequences, each one of which recognizes only one amplification product. Such schemes offer significant advantages in reducing ambiguities caused by differential responses in different animals.

Example 9 In Vivo Testing.

Initially, normal CD-1 male mice (Charles River, Willmington, Mass.) are used to investigate the clearance and biodistribution of $^{111}$In-labeled oligonucleotides and complexes over time. These studies provide an indication of the ideal timing for the second and subsequent injections.

To demonstrate tumor amplification, Balb/c nu/nu nude mice (Taconic Labs; Germantown, N.Y.) are inoculated with one of the breast tumor cell lines described previously. Animals are used when tumors are about 1 cm in their largest dimension. Since an antibody is to serve as the initial injectate, preliminary studies include evaluation for the binding efficiency of labeled antibody to the tumor in this mouse model and the ideal dose of antibody. Once established, the two amplification systems are evaluated. The degree of amplification achieved at the tumor relative to blood and other issues is evaluated using the conventional approach with directly labeled antibodies.

Example 10 Preparation of Multimeric Nucleic Acid Constructs.

Multimeric nucleic acid constructs were prepared from the 24-mer M13mp18 reverse sequencing primers obtained biotinylated and lyophilized from Operon Technologies (Alameda, Calif.). A column of 2-iminobiotin agarose (Sigma Chemical; St. Louis, Mo.) was prepared in buffer (50 mM $Na_2CO_3$, pH 11/1M NaCl). Streptavidin (Boehringer Mannheim Biochemicals, Indianapolis, Ind.) at 50 ug/ml was applied to the column for 10 minutes at 4° C. Total volume of the column was about 2 mls. Reconstituted reverse sequencing primers, about 2 mls, were applied to the column at about 40 ug/ml in buffer. The column was washed with 8 mls of buffer and eluted with 50 mM $NH_4OAc$/6M urea, pH 4, into ten 500 ul fractions. The absorbance (260 mm) of a 20 ul aliquot of each fraction was taken (Table 1).

TABLE 1

| Fraction No. | Absorbance 260 | Fraction No. | Absorbance 260 |
|---|---|---|---|
| 1 | 0.002 | 6 | 0.006 |
| 2 | 0.003 | 7 | 0.005 |
| 3 | 0.009 | 8 | 0.004 |
| 4 | 0.012 | 9 | 0.003 |
| 5 | 0.009 | 10 | 0.003 |

Figure 4:
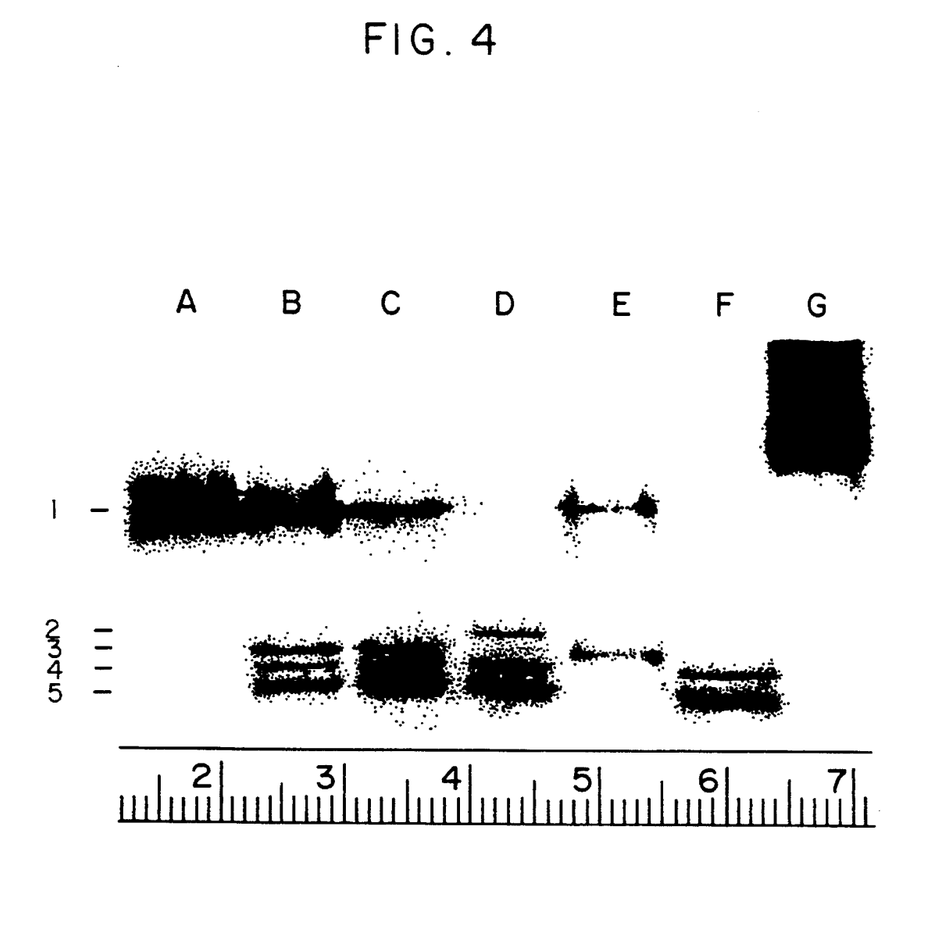
FIG. 4 Nondenaturing polyacrylamide gel electrophoresis of multimeric DNA complexes.

Fractions 2–9 were pooled and the mixture concentrated and buffer exchanged using ultrafiltration with 30,000 molecular weight cutoff membrane into 10 mM Tris, pH 7.5/1 mM EDTA. A sample from the pooled fractions was electrophoresed into an 8.5% nondenaturing, polyacrylamide gel (FIG. 4; lane E). After electrophoresis, the gel was stained with coomassie brilliant blue (Sigma Chemical; St. Louis, Mo.) and photographed (FIG. 4). Lane A is a sample of pure streptavidin (1.25 mg/ml) to indicate its position in the gel (FIG. 4; position 1). Lane B is an identical amount of streptavidin plus one equivalent (36 pmol/ul) of biotinylated DNA (reverse sequencing primer) incubated together to test for formation of multiple species of constructs. As observed, some free streptavidin is present and at least three and possibly four forms of constructs can be identified (FIG. 4, positions 2, 3, 4, 5). Under nondenaturing condition species with greater numbers of DNA molecules are expected to migrate faster due to the increased ionic character. Lanes C and D are similar samples wherein 3 (100 pmol/ul) and 14 (500 pmol/ul) equivalents of biotinylated DNA, respectively, were added to streptavidin. Band intensity becomes biased toward the faster moving species with increasing amounts of DNA. Lane E is a sample of the pooled fraction from the column showing predominantly one band (about 0.5 ug/ul). Lanes F and G are similar column samples with the addition of 4 equivalents (150 pmol/ul) of biotinylated DNA and biotinylated IgG (about 5.0 ug/ul), respectively, to test the ability of multimeric nucleic acid constructs to bind both nucleic acids and proteins. These experiments demonstrate that multimeric nucleic acid constructs can be created with predetermined numbers of nucleic acid species and that constructs retain further binding ability.

Example 11 Amplification of Radioactivity using Complementary DNA Conjugates.

Biotinylated 22-mer single-stranded DNAs were bound to avidin. Two complementary DNA sequences were used resulting in two complementary DNA-avidin constructs referred to as "A" and "B". A was labeled with $^{125}$I prepared using thallic ion as an oxidant. B was added to radiolabeled A and subjected to size exclusion analysis with a shift in radioactivity into a higher molecular weight form demonstrating that hybridization had occurred. No shift was evident when A was added to radiolabeled A.

To demonstrate amplification, B was added to radiolabeled A at an 8:1 (B:A) molar ratio. Analysis by HPLC showed broad peaks and a shift from 80 Kd to about 320 Kd. By radioactivity and colorimatic estimates of protein concentration, this species was identified as a 3:1 (B:A) tetramer. Finally, radiolabeled A was added to the tetrameric fraction at a 6:1 (A:B) molar ratio. This resulted in a large shift in molecular weight to the void as expected for a large aggregate. These experiments demonstrate in vitro amplification by successive additions of complementary DNA-avidin constructs.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

We claim:

1. A self-assembling aggregate comprising a construct comprising a first streptavidin or avidin molecule, having a plurality of first biotinylated single-stranded nucleic acids bound to said first streptavidin or avidin molecule;

a plurality of second biotinylated single-stranded nucleic acids bound to a second streptavidin or avidin molecule to form a multimeric nucleic acid, at least one of said second nucleic acids hybridizing with a complementary sequence of one of said first nucleic acids; and a functional group attached to a third single-stranded nucleic acid, said third single-stranded nucleic acid hybridizing with complementary sequence of one of said second single-stranded nucleic acids bound to said multimeric nucleic acid.

2. The aggregate of claim 1 wherein the nucleic acids are selected from the group consisting of DNA, RNA and PNA (polyamide nucleic acid).

3. The aggregate of claim 1 wherein the nucleic acids are between 5 to 50 nucleotides in length.

4. The aggregate of claim 1 wherein the nucleic acids are between 8 to 25 nucleotides in length.

5. The aggregate of claim 1 wherein each of the plurality of first nucleic acids are identical.

6. The aggregate of claim 1 further comprising a biotinylated antibody bound to said first streptavidin or avidin molecule.

7. The aggregate of claim 1 wherein the functional group is selected from the group consisting of radioisotopes, pharmaceutically active moieties, genes, gene fragments, antigens, antibodies, antibody fragments, and combinations thereof.

8. The aggregate of claim 1, wherein the functional group is selected from the group consisting of toxins, cytokines metals, metabolic analogs, enzymes, oxidizing agents, bacteriostatic and bacteriocidal agents, and combinations thereof.

9. The aggregate of claim 1 wherein the functional group is selected from the group consisting of proteins, peptides, and nucleic acids, and combinations thereof.

10. A self-assembling aggregate comprising a first construct comprising a plurality of first single-stranded nucleic acids bound to a first coupling agent forming a first multimer;

a second construct comprising a plurality of second single-stranded nucleic acids bound to a second coupling agent forming a second multimer, at least one of said second single-stranded nucleic acids hybridizing with a complementary sequence of one of said first single-stranded nucleic acids; and a plurality of third single-stranded nucleic acids, each of said third single-stranded nucleic acids being attached to a functional group, and each of said third single-stranded nucleic acids hybridizing with a complementary sequence of a single-stranded nucleic acid attached to the aggregate, wherein the first counting agent and the second coupling agent each include a protein, a 5'-amino-containing oligonucleotide, a 5'-thiol-containing oligonucleotide, a polyamidoamine or a divalent linker.

11. The aggregate of claim 10 wherein at least one of the first coupling agent and the second coupling agent is a protein selected from the group consisting of streptavidin, avidin, antibodies, protein A chimeras, and specific binding fragments thereof, the respective first or second single-stranded nucleic acids being conjugated to a moiety specifically bound by said protein or fragment.

12. The aggregate of claim 10, wherein the first construct and the second construct each comprise from three to seven single-stranded nucleic acids.

13. The aggregate of claim 10, wherein the plurality of third single-stranded nucleic acids do not hybridize with any nucleic acid bound to said first coupling agent.

14. The aggregate of claim 10, wherein at least one of the first coupling agent and the second coupling agent is selected from the group consisting of 5'-amino-containing oligonucleotides, 5'-thiol-containing oligonucleotides and polyamidoamines.

15. The aggregate of claim 10 wherein at least one of the first coupling agent and the second coupling agent are selected from the group consisting of streptavidin and avidin.

16. The aggregate of claim 10, wherein at least one of the first construct and the second construct is a dendrimer.

* * * * *

UNITED STATES PATENT AND TRADEMARK OFFICE
CERTIFICATE OF CORRECTION

PATENT NO. : 5,561,043
DATED : October 1, 1996
INVENTOR(S) : Charles R. Cantor et al.

It is certified that error appears in the above-identified patent and that said Letters Patent is hereby corrected as shown below:

Title page,
Item [73], Assignee, replace "Trustees of Boston University, Boston, Mass" with -- Trustees of Boston University, Boston, MA and Univeristy of Massachusetts, Worcester, MA --

Signed and Sealed this

Sixteenth Day of March, 2004

JON W. DUDAS
*Acting Director of the United States Patent and Trademark Office*